(12) United States Patent
Johansen et al.

(10) Patent No.: US 8,876,779 B2
(45) Date of Patent: *Nov. 4, 2014

(54) AUTO INJECTOR WITH CHANGING ANCHOR LOCATIONS FOR A MECHANICAL DRIVER

(75) Inventors: Esben Weldingh Johansen, Struer (DK); Jørgen Rasmussen, Struer (DK); Christian Maegaard, Kerteminde (DK); Jørn Winther Hald, Struer (DK)

(73) Assignee: Bang & Olufsen Medicom A/S, Struer (DK)

( * ) Notice: Subject to any disclaimer, the term of this patent is extended or adjusted under 35 U.S.C. 154(b) by 1078 days.

This patent is subject to a terminal disclaimer.

(21) Appl. No.: 12/742,295

(22) PCT Filed: Nov. 12, 2008

(86) PCT No.: PCT/DK2008/000400
§ 371 (c)(1),
(2), (4) Date: May 11, 2011

(87) PCT Pub. No.: WO2009/062509
PCT Pub. Date: May 22, 2009

(65) Prior Publication Data
US 2011/0224621 A1    Sep. 15, 2011

Related U.S. Application Data

(60) Provisional application No. 60/996,344, filed on Nov. 13, 2007.

(30) Foreign Application Priority Data

Nov. 12, 2007  (DK) .................................. 2007 01596
Dec. 21, 2007  (DK) .................................. 2007 01867
Dec. 21, 2007  (DK) .................................. 2007 01869
Dec. 21, 2007  (DK) .................................. 2007 01870

(51) Int. Cl.
*A61M 5/32* (2006.01)
*A61M 5/20* (2006.01)

(52) U.S. Cl.
CPC .......... *A61M 5/2033* (2013.01); *A61M 5/3287* (2013.01); *A61M 5/326* (2013.01); *A61M 2005/206* (2013.01); *A61M 2005/2013* (2013.01); *A61M 2005/208* (2013.01)
USPC ........... 604/198; 604/211; 604/135; 604/136; 604/890.1

(58) Field of Classification Search
USPC .................... 604/135–136, 211, 890.1, 198
See application file for complete search history.

(56) References Cited

U.S. PATENT DOCUMENTS

| 2,605,766 A | 8/1952 | Uytenbogaart |
| 4,681,566 A | 7/1987 | Fenton, Jr. et al. |
| 5,267,963 A | 12/1993 | Bachynsky |
| 6,270,479 B1 | 8/2001 | Bergens et al. |

(Continued)

FOREIGN PATENT DOCUMENTS

| CN | 1917912 A | 2/2007 |
| DE | 1038718 B | 9/1958 |

(Continued)

*Primary Examiner* — Edelmira Bosques
(74) *Attorney, Agent, or Firm* — Volentine & Whitt, PLLC

(57) ABSTRACT

The present invention relates to a disposable auto injector that can be safely operated for automatic injection of a dose of medication and having a housing for accommodation of a syringe with a needle, the syringe being movably positioned in the housing between a first position in which position the needle is accommodated inside the housing and a second position in which position the needle protrudes outside the housing, a mechanical driver anchored to the housing at a first anchor location for applying a force to the syringe thereby moving the syringe from the first position to the second position, and wherein the mechanical driver is also configured for applying a force to the syringe by anchoring the mechanical driver to a different second anchor location.

15 Claims, 20 Drawing Sheets

(56) References Cited

U.S. PATENT DOCUMENTS

Figure 1:
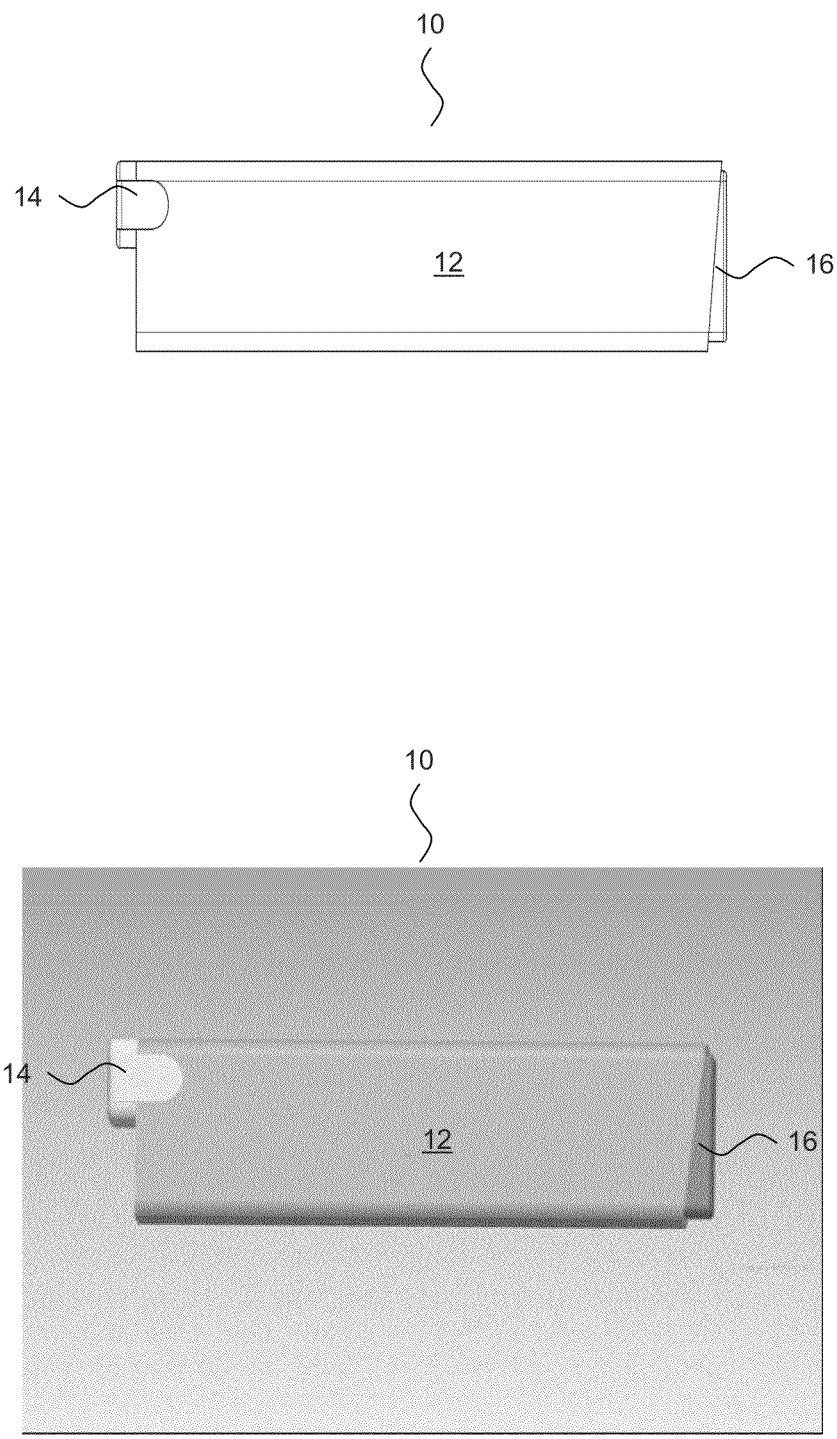

| | | |
|---|---|---|
| 7,442,185 B2 | 10/2008 | Amark et al. |
| 7,678,072 B2 | 3/2010 | Weber |
| 2002/0095120 A1 | 7/2002 | Larsen et al. |
| 2003/0105430 A1 | 6/2003 | Lavi et al. |
| 2004/0039336 A1 | 2/2004 | Amark et al. |
| 2004/0064096 A1 | 4/2004 | Flaherty et al. |
| 2007/0027430 A1 | 2/2007 | Hommann |
| 2009/0312707 A1 | 12/2009 | Bishop et al. |

FOREIGN PATENT DOCUMENTS

| | | |
|---|---|---|
| DE | 202005014958 U1 | 12/2005 |
| EP | 0666084 A3 | 8/1997 |
| EP | 1349590 | 10/2003 |
| EP | 1349590 A | 10/2003 |
| WO | WO 86/01120 A1 | 2/1986 |
| WO | WO 01/30425 A1 | 5/2001 |
| WO | 0217996 A1 | 3/2002 |
| WO | 0247746 A1 | 6/2002 |
| WO | 02051471 A1 | 7/2002 |
| WO | 03099358 A2 | 12/2003 |
| WO | WO 2005/009515 A1 | 2/2005 |
| WO | 2005058396 A1 | 6/2005 |
| WO | WO 2005/097238 A2 | 10/2005 |
| WO | WO 2006/052737 A1 | 5/2006 |
| WO | 2007002053 A2 | 1/2007 |
| WO | WO 2007/033638 A1 | 3/2007 |
| WO | 2007129324 A3 | 11/2007 |

AUTO INJECTOR WITH CHANGING ANCHOR LOCATIONS FOR A MECHANICAL DRIVER

CROSS REFERENCE TO RELATED APPLICATIONS

This application is the national phase under 35 U.S.C. 371 of PCT International Application No. PCT/DK2008/000400 which has an international filing date of Nov. 12, 2008, and also claims priority under 35 U.S.C. 119 to Danish application PA 2007 01596 filed on Nov. 12, 2007, to U.S. provisional application 60/996,344 filed on Nov. 13, 2007, to Danish application PA 2007 01867 filed on Dec. 21, 2007, to Danish application PA 2007 01869 filed on Dec. 21, 2007, and to Danish application PA 2007 01870 filed on Dec. 21, 2007, which applications are hereby incorporated by reference in their entirety for all purposes as if fully set forth herein.

The present invention relates to a disposable auto injector that can be safely operated for automatic injection of a dose of medication.

EP 1 349 590 discloses an auto injector with a housing that accommodates a syringe with a needle and has a needle cover surrounding the needle. Further, the housing accommodates spring means capable of, upon activation, pushing the needle through the needle cover as well as injecting the dose of medication. The auto injector further has first locking means capable of locking the spring means in a compressed state, and first activating means capable of upon manual operation, releasing the spring means for injection. The first activating means can not be operated unless a contact part of the injector is actually pressed against the injection site. Thus, it is required to perform a two-step operation in order to inject the medication whereby inadvertent triggering of the auto injector is avoided.

In other prior art auto injectors, the syringe with the needle is retracted into the housing so that the needle does not protrude from the housing upon removal of the injector from the injection site. For this purpose, prior art devices typically comprise two coil springs, a first spring for moving the syringe to a position wherein the needle protrudes from the housing, and a second spring for retracting the syringe with the needle into the housing. The second spring must be sufficiently strong to overcome the force of the first spring.

Thus, there is a need for an alternative design of an auto injector.

According to the present invention, the above-mentioned and other objects are fulfilled by provision of an auto injector with a housing for accommodation of
a syringe with a needle, the syringe being movably positioned in the housing between a first position in which position the needle is accommodated inside the housing and a second position in which position the needle protrudes outside the housing,
a mechanical driver anchored to the housing at a first anchor location for applying a force to the syringe thereby moving the syringe from the first position to the second position, characterized in that
the mechanical driver is also configured for applying a force to the syringe by anchoring the mechanical driver to a different second anchor location.

In one embodiment, the mechanical driver is configured for moving the syringe from the second position to a retracted position in which position the needle is accommodated inside the housing, when the mechanical driver is anchored to the second anchor location.

Utilisation of a single mechanical driver for moving the syringe in a forward direction from its first position to its second position and also for moving the syringe in the opposite direction from its second position to its retracted position provides a simple drive mechanism for retraction of the syringe into the housing after the injection is provided.

The mechanical driver may be positioned laterally in relation to the syringe.

Alternatively, the mechanical driver may be arranged in an end to end relationship with the syringe, for example with a coil spring extending along the longitudinal axis of the syringe.

The mechanical driver may be arranged in a coaxial relationship with the syringe, for example such that components of the injector are arranged both inside a coil spring constituting the mechanical driver and outside the coil spring for provision of a compact construction.

The auto injector may further comprise a rotatable release shaft rotatably mounted in the housing between at least two angular positions, preferably between at least three angular positions, for control of the sequence of operation of the auto injector.

The auto injector may further comprise a first injection lock that is configured in a locked state for preventing syringe movement from the first position to the second position and an injection trigger member is configured for releasing the first injection lock to an unlocked state by user operation of the injection trigger member in which unlocked state the first injection lock does not prevent the driver from moving the syringe from the first position to the second position.

Advantageously, the first injection lock may comprise the rotatable release shaft mounted in the housing for rotation between a first angular position in which position movement of the syringe from the first position to the second position is prevented and a second angular position in which position movement of the syringe from the first position to the second position is not prevented.

Utilization of a rotatable shaft for controlling displacement of parts in the injector by locking the position of specific parts in one angular position of the shaft and unlocking the position of the specific parts in another angular position of the shaft makes the device more resistant to possible user dropping of the device.

In prior art devices, locking and unlocking displacement of parts in the auto injector by linear movement of locking parts is inherently sensitive to dropping of the device, since such dropping may induce a linear movement of parts in the device, e.g. causing inadvertent triggering of the device. In the auto injector according to the invention, dropping of the device will not turn the rotatable shaft, and since the auto injector can not be dropped on the injection trigger member and the release member simultaneously, the device will not inadvertently be triggered by dropping of the device.

Preferably, the rotatable release shaft is positioned laterally in relation to the syringe.

The mechanical driver may be a spring, such as a coil spring, a constant force spring, etc.

The spring may be arranged coaxially with the rotatable release shaft for further size reduction of the injector.

In an embodiment of the present invention, the injection trigger member is coupled to the rotatable release shaft and configured to turn the release shaft from the first angular position to the second angular position by user operation.

For example, the injection trigger member may have a flange that abuts a tap protruding from the release shaft perpendicular to the longitudinal axis of the release shaft in such a way that movement of the injection trigger member with the flange displaces the tap thereby turning the release shaft an angle from the first angular position to the second angular position.

The injector may further comprise a movable member configured with a first ring positioned in such a way that the release shaft extends through the first ring, and wherein the release shaft has first tongues protruding from the release shaft and extending in parallel with the longitudinal axis of the release shaft with end edges abutting the first ring in one angular position of the release shaft thereby preventing the first ring from moving in the direction of the first tongues.

The first ring may have through-going grooves in its inner circular circumferential surface abutting the release shaft positioned in such a way that the first tongues of the release shaft in another angular position of the release shaft fit respective through-going grooves in the inner circular circumferential surface of the first ring, the grooves being sized to accommodate the tongues thereby allowing the first ring to slide along the release shaft with the tongues sliding in the grooves so that the first ring can be displaced in the direction of the first tongues.

The movable member may comprise a first arm connected to the first ring for conveying a force from the driver to the syringe plunger end for moving the syringe from the first position to the second position.

For example, in the first angular position of the release shaft, the driver may urge the first ring against the edges of the first tongue whereby the syringe is kept in its first position, while in the second angular position, the first tongues fit respective through-going grooves in the first ring so that the first ring is allowed to slide along the release shaft driven by the driver whereby the syringe is moved to its second position.

Preferably, the driver is further configured for pushing the syringe plunger further into the syringe thereby supplying a dose of medicament contained in the syringe.

In the housing of the auto injector, two parts are laterally positioned in relation to each other when they are positioned by the side of each other. For example, two elongated parts, each of which extends along a longitudinal axis, are laterally positioned in relation to each other when their individual longitudinal axes do not coincide.

The lateral arrangement of the syringe with relation to the driver and the rotatable release shaft makes it possible to mount the syringe in the device at various selected stages of assembly of the auto injector. For example, it is possible to assemble the auto injector at one site and subsequently mount the syringe with the medicament at another site which again makes it possible for a pharmaceutical company to buy an assembled auto injector for use with their own syringe with medicament so that handling of the syringe with medicament is kept within the premises of the pharmaceutical company.

Further, the lateral arrangement leads to the advantage that space is available in the housing of the auto injector for accommodation of drivers of various sizes and shapes and thus, different models of the auto injector fulfilling different requirements may be provided with limited effort.

For example, in an embodiment with a coil spring driver, coil springs of different thickness and number of turns and shape, e.g. conical coil springs, etc, may be arranged in the housing of the auto injector for provision of different forces, displacements, and forces varying as a predetermined function of time, etc, suitable for different types of injections.

In a prior art injector, components of the injector are arranged both inside the coil spring and outside the coil spring so that geometrical dimensions of the coil spring can not easily be changed in order to obtain another force and/or displacement by the coil. The lateral arrangement according to the invention makes it possible to utilize drivers of different geometries.

The auto injector may further be configured for user operation in a certain sequence in which triggering of an injection is only possible for example when the injector is pressed against the injection site.

Thus, the auto injector may further comprise a second injection lock configured in a locked state for preventing syringe movement from the first position to the second position by user operation of the injection trigger member and a release member configured for releasing the second injection lock to an unlocked state by first user operation of the release member in which unlocked state the second injection lock does not prevent syringe movement from the first position to the second position by user operation of the injection trigger member.

The release member may be configured for abutment with the injection site during use, and first user operation may be constituted by the user pressing the release member against the injection site.

The second injection lock may be configured in the locked state to prevent user operation of the injection trigger member.

The auto injector may further be configured for automatically retracting the needle back into the housing upon termination of injection of medication, for example immediately upon removal of the auto injector from the injection site, in order to avoid inadvertent contact with the used needle.

Thus, the auto injector may further comprise a retraction lock for prevention of retraction of the syringe in a locked state.

The release member may further be configured for releasing the retraction lock to an unlocked state by second user operation of the release member thereby allowing the driver to retract the syringe.

The second user operation of the release member may be constituted by the user removing the release member from the injection site.

The driver may further be configured for retracting the syringe from the second position to a retracted position in which the needle does not protrude from the housing.

The release shaft may further be configured for rotation between a third angular position in which position the shaft prevents movement of the syringe from the second position to the retracted position and a fourth angular position in which position the shaft does not prevent movement of the syringe from the second position to the retracted position.

The release shaft may further have second tongues protruding from the release shaft and extending in parallel with the longitudinal axis of the release shaft and displaced along the longitudinal axis of the release shaft in relation to the first tongues with end edges abutting a second ring in the other angular position of the release shaft thereby preventing the second ring from moving in the direction of the second tongues. Thus, the end edges of the tongues abutting the second ring form the first anchor location. Through-going grooves of the second ring fit respective second tongues in a third angular position of the release shaft and the grooves are sized to accommodate the second tongues thereby allowing the second ring to slide along the release shaft with the second tongues sliding in the grooves so that the second ring can be displaced in the direction of the second tongues.

The third angular position may be identical to the second angular position.

The auto injector may further comprise a second arm connected to the second ring for conveying a force from the driver to the syringe shoulder for retracting the syringe from the second position to the retracted position.

Figure 2:
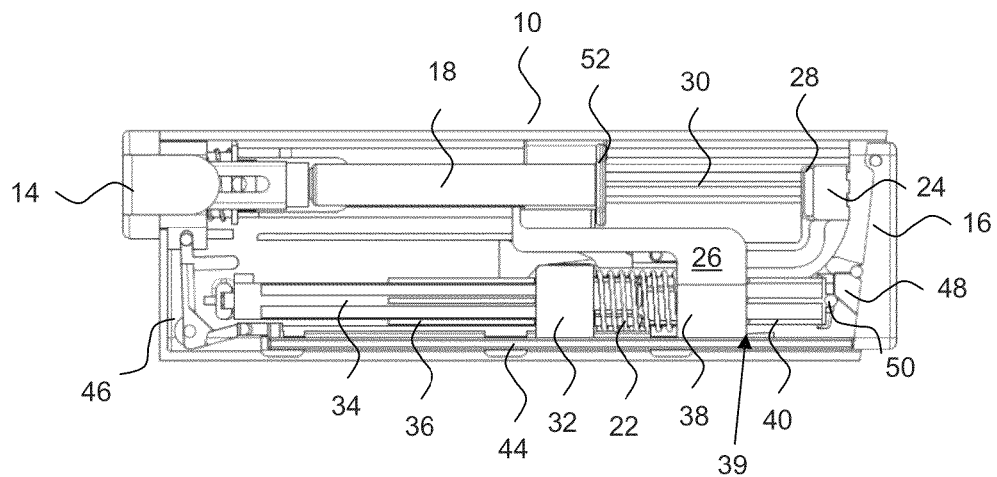
Figure 2:
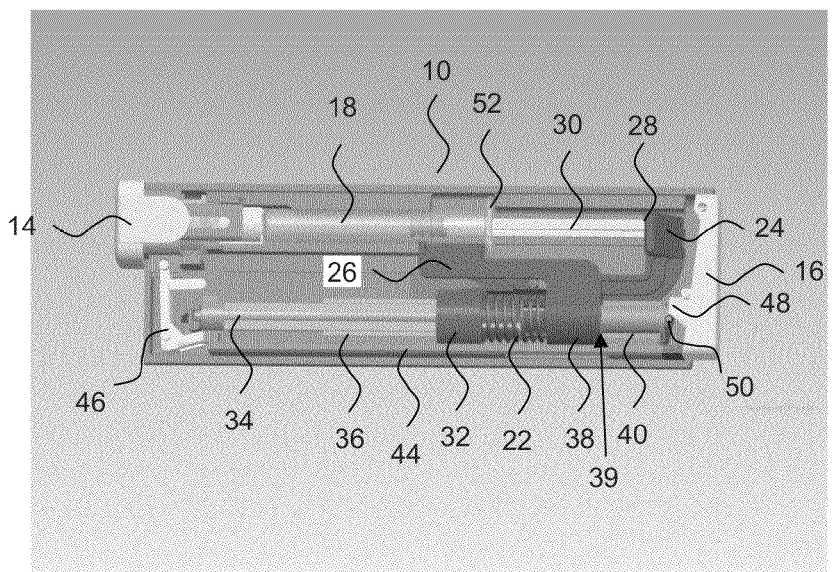
Figure 3:
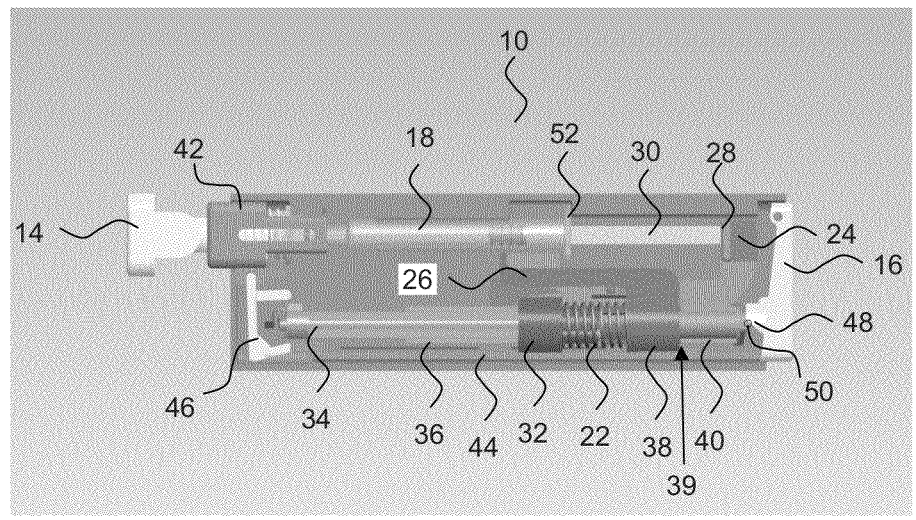
Figure 4:
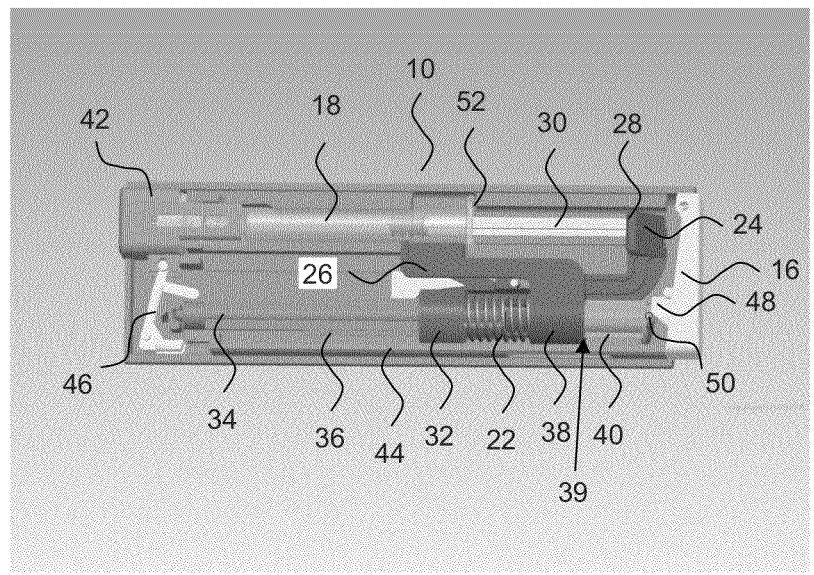
Figure 5:
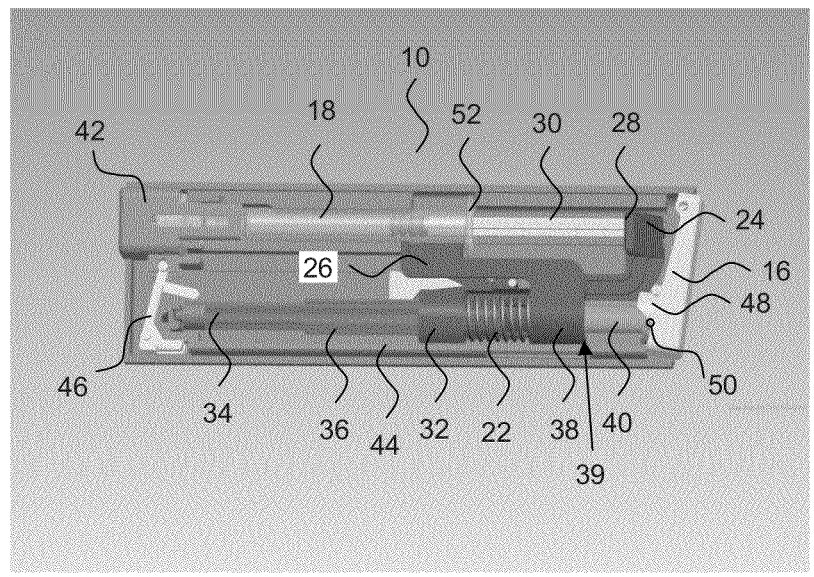
Figure 6:
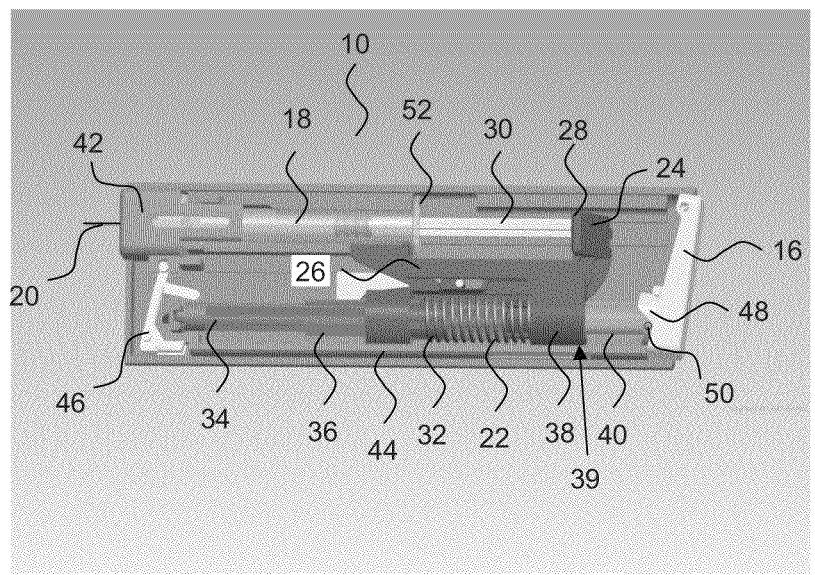
Figure 7:
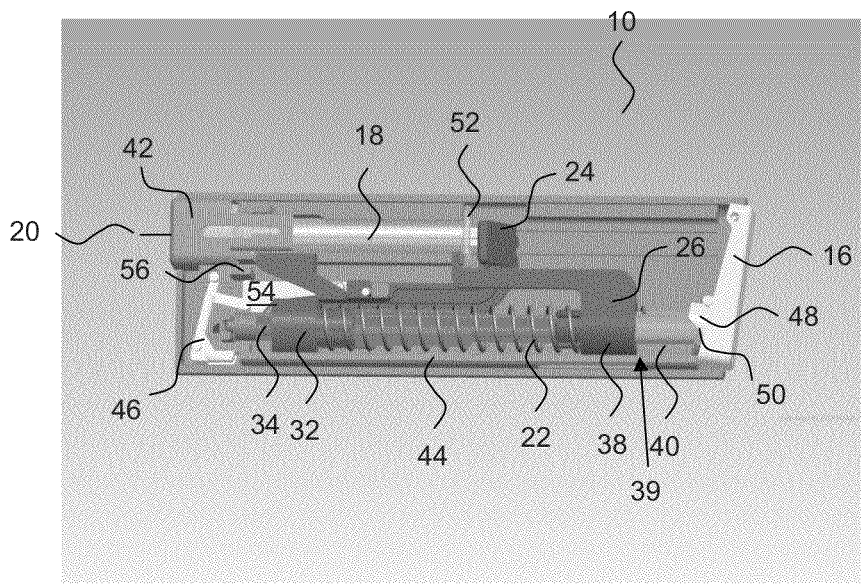
Figure 8:
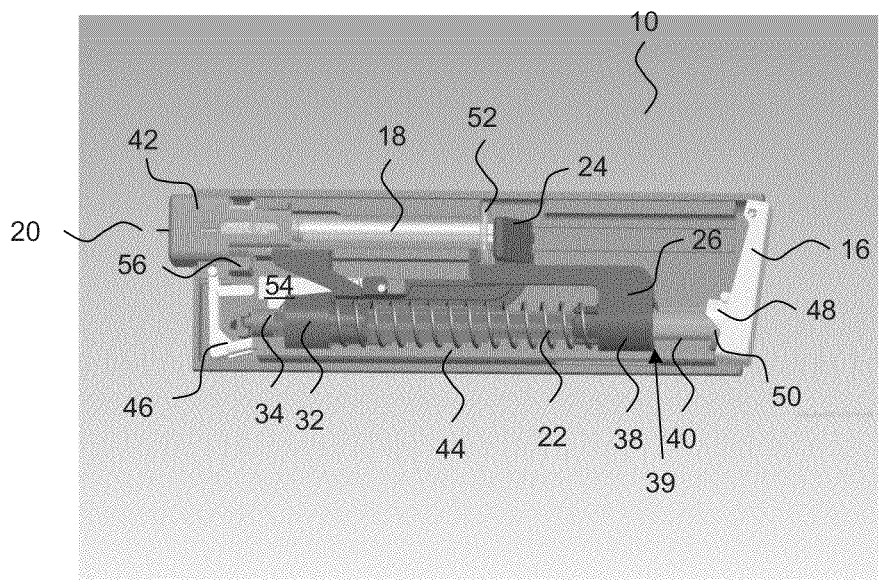
Figure 9:
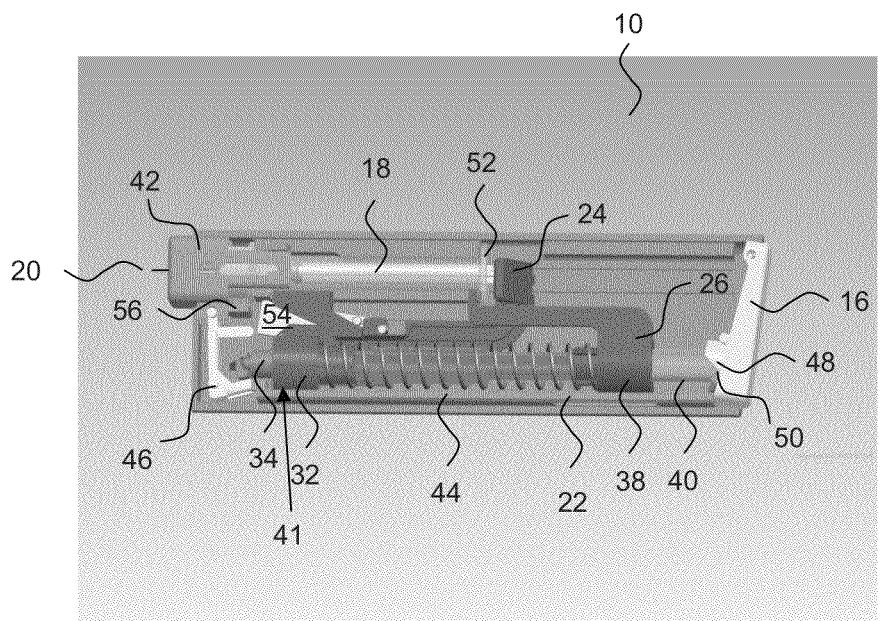
Figure 10:
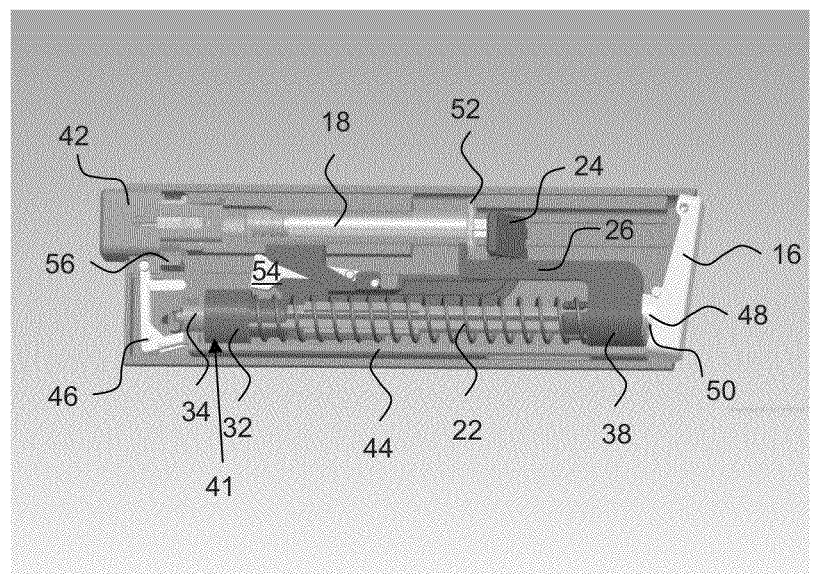
Figure 11:
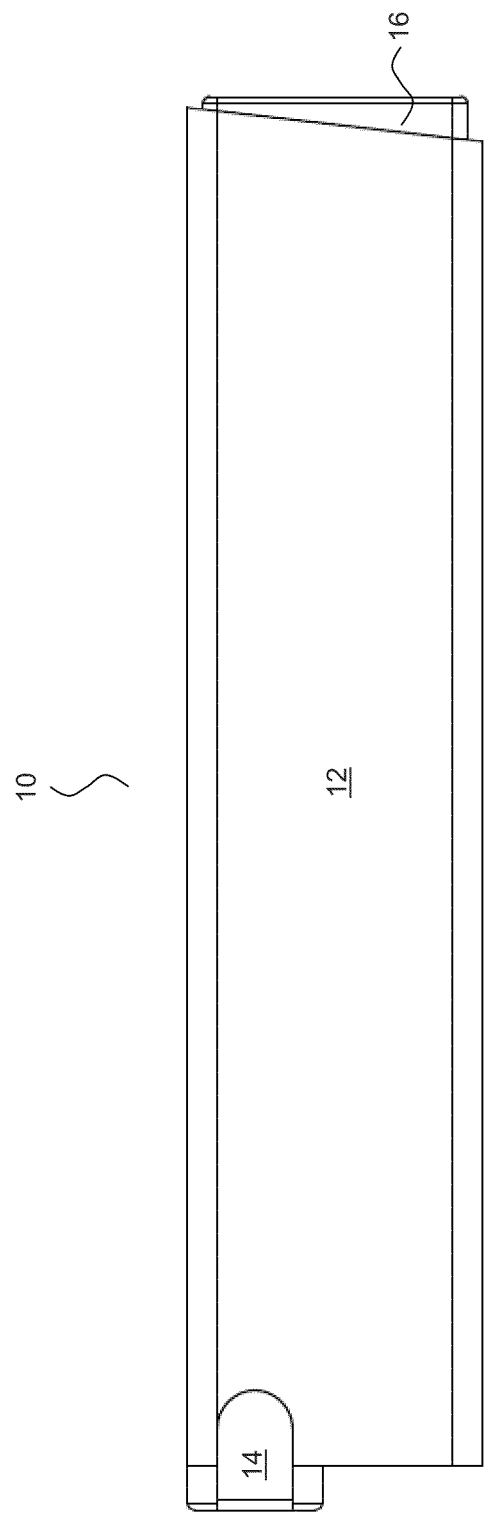
Figure 12:
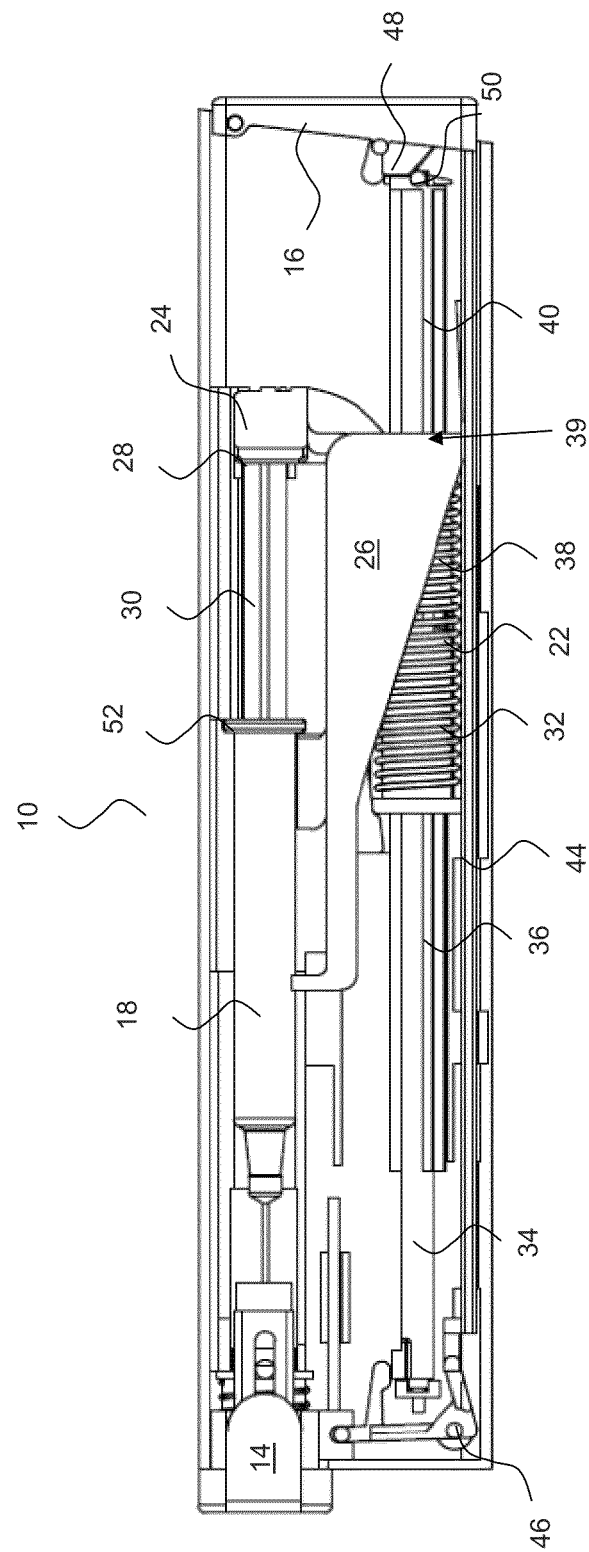
Figure 13:
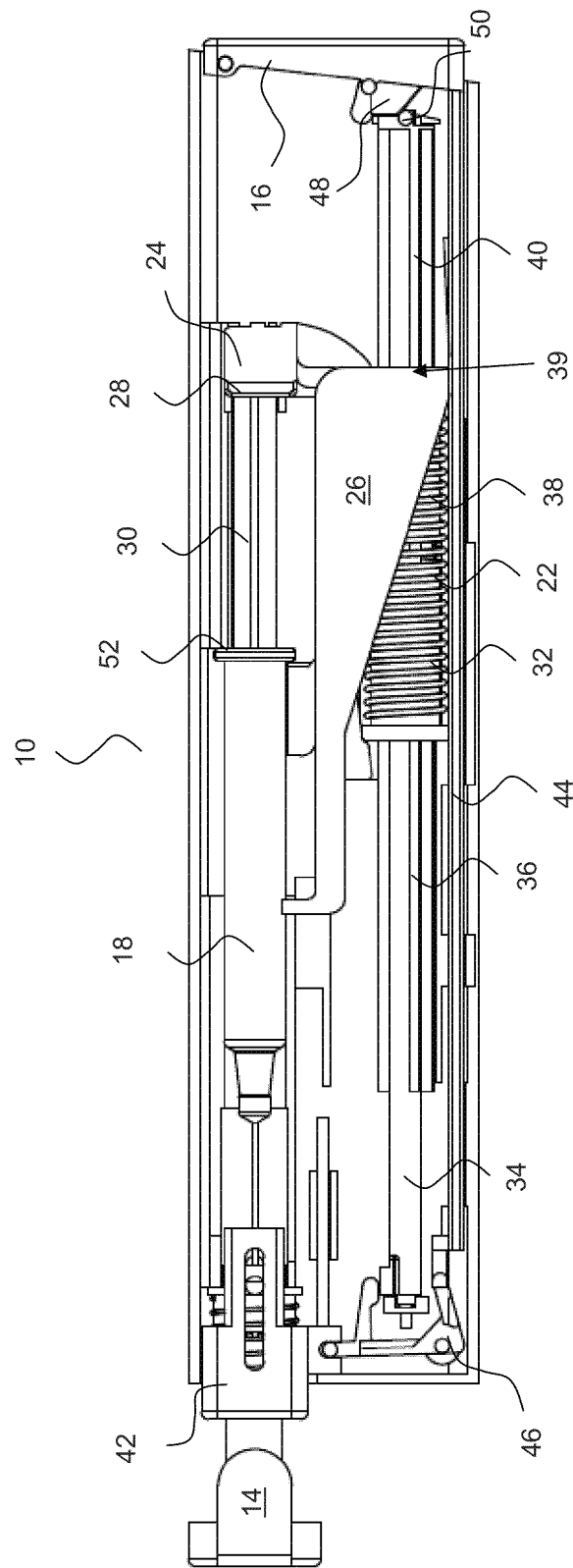
Figure 14:
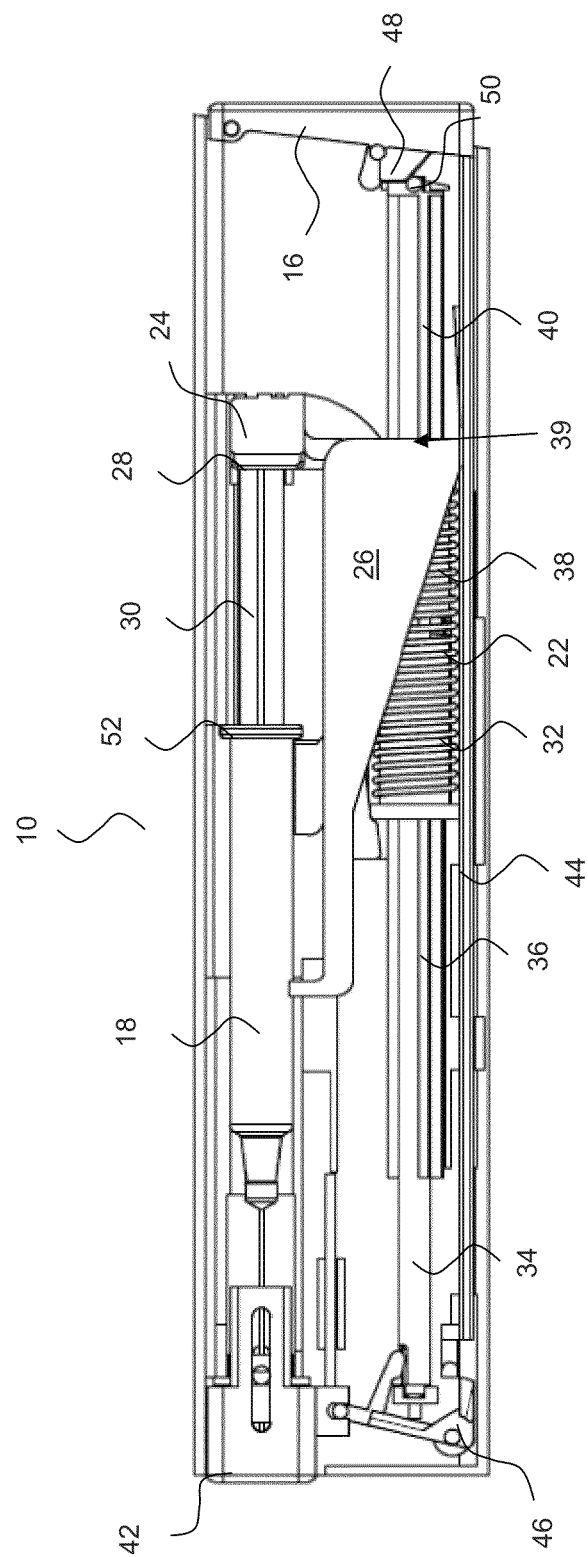
Figure 15:
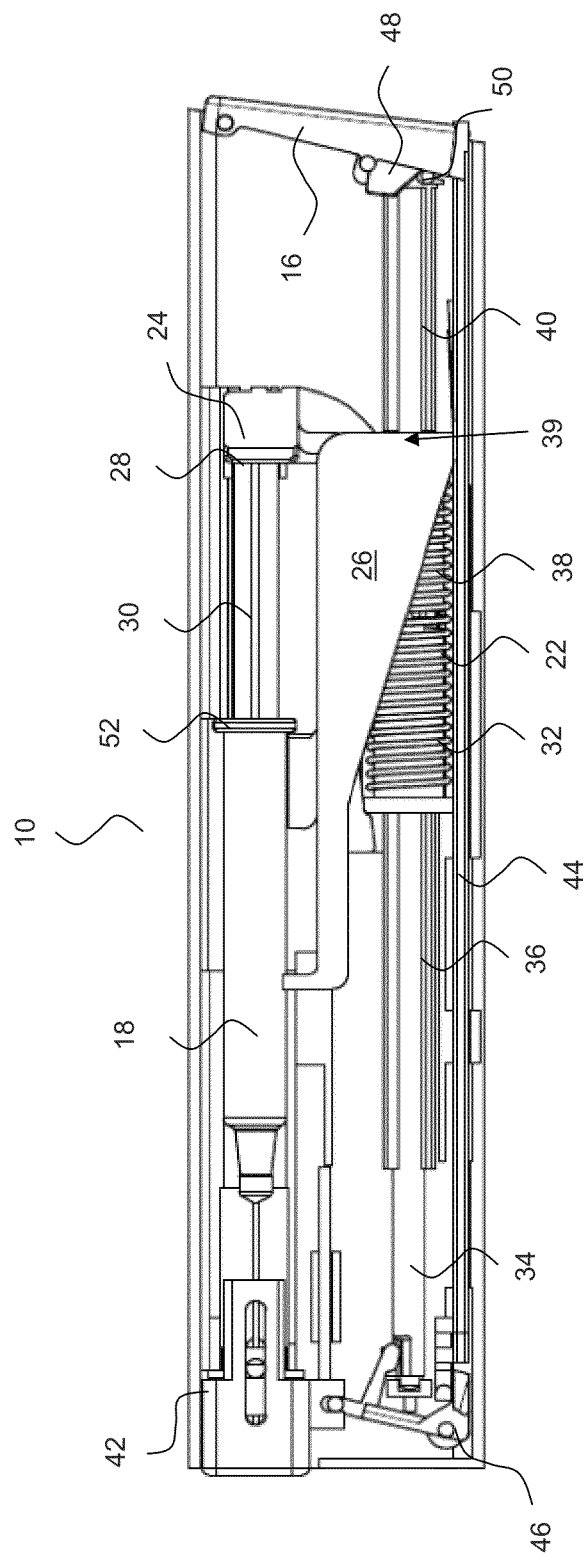
Figure 16:
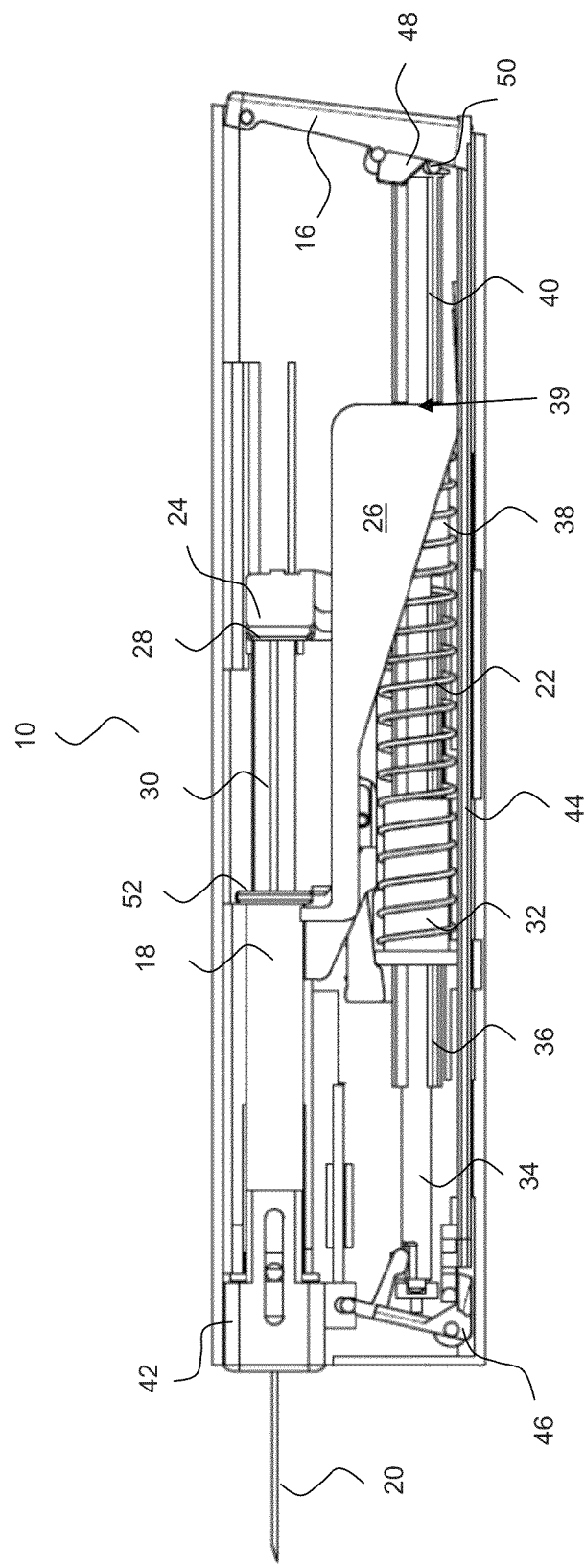
Figure 17:
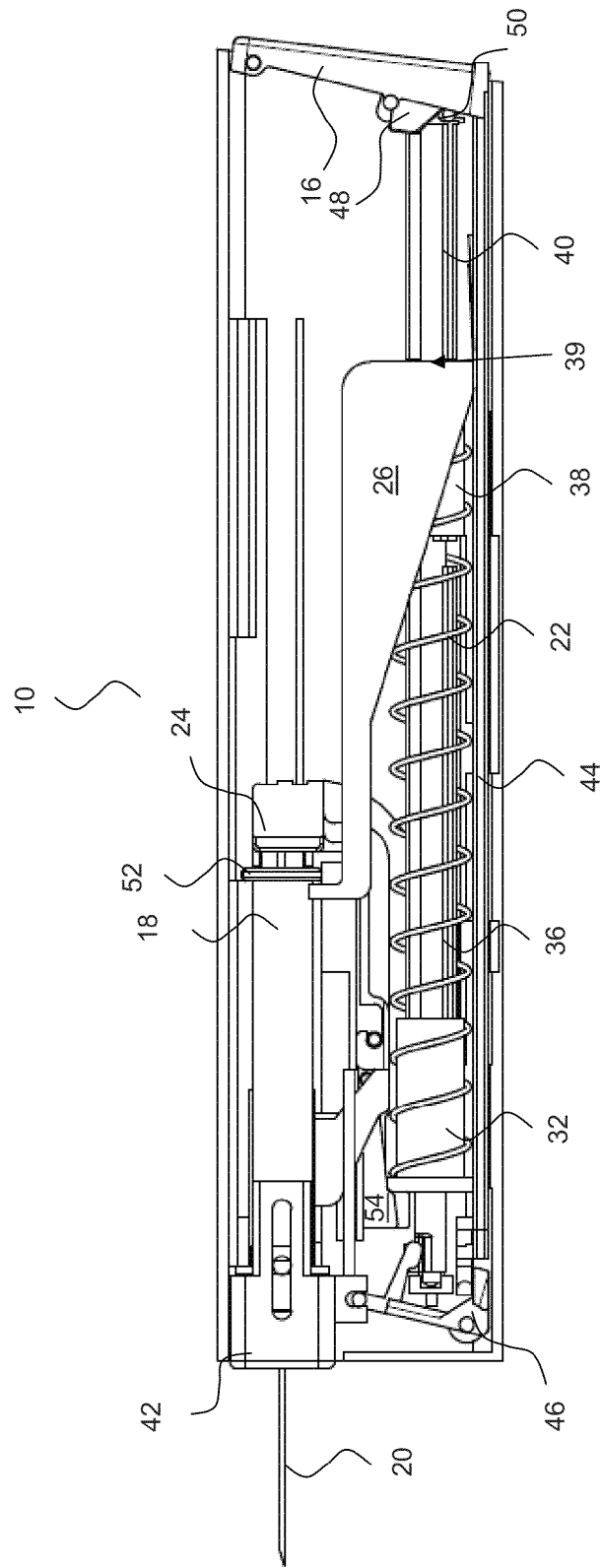
Figure 18:
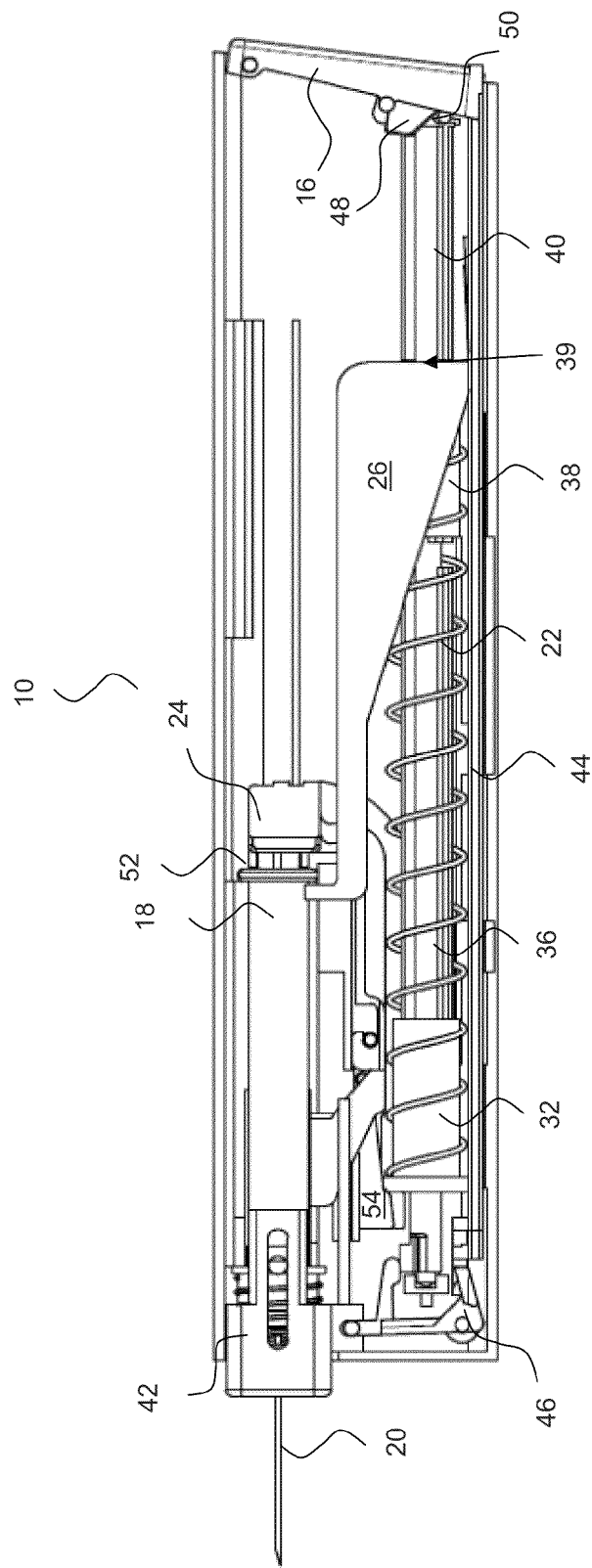
Figure 19:
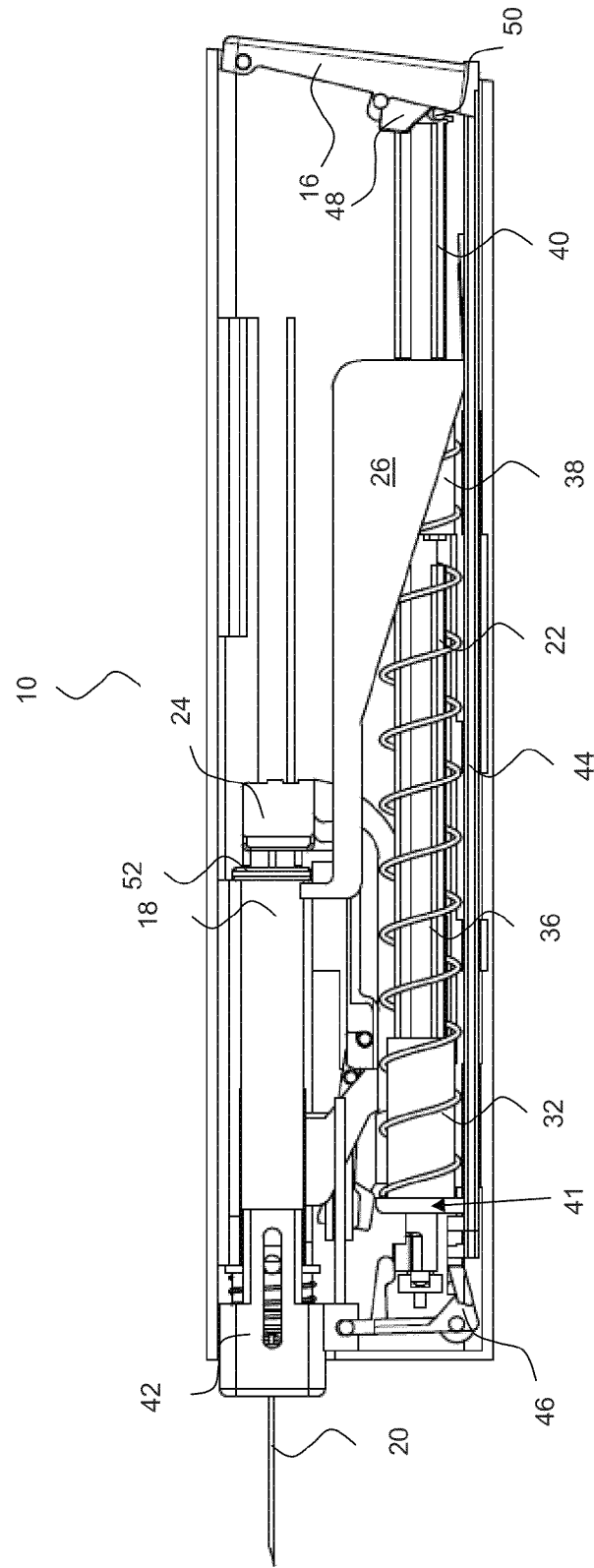
Figure 20:
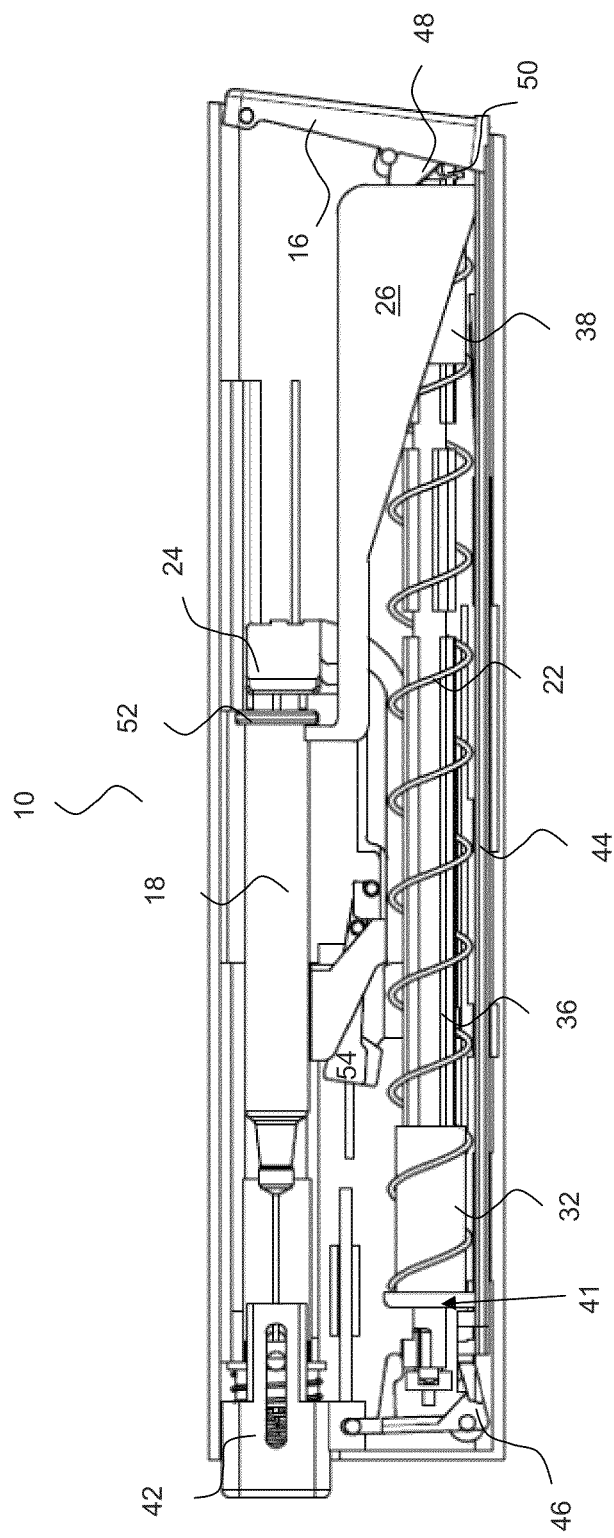

The above and other features and advantages of the present invention will become readily apparent to those skilled in the art by the following detailed description of exemplary embodiments thereof with reference to the attached drawings, in which:

FIG. 1 shows an auto injector according to the invention with a protection cap,

FIG. 2 shows the auto injector of FIG. 1 in a state ready for use and with a part of the housing cut away, FIG. 3 shows the auto injector of FIG. 2 with the protection cap removed, FIG. 4 shows the auto injector of FIG. 2 with the release member activated, FIG. 5 shows the auto injector of FIG. 2 with the injection trigger member activated, FIG. 6 shows the auto injector of FIG. 2 with the syringe moved to its second position, FIG. 7 shows the auto injector of FIG. 2 with the syringe emptied, FIG. 8 shows the auto injector of FIG. 2 with the release member released, FIG. 9 shows the auto injector of FIG. 2 with the retraction lock released, FIG. 10 shows the auto injector of FIG. 2 with the syringe retracted, FIG. 11 shows an auto injector according to the invention with a protection cap, FIG. 12 shows the auto injector of FIG. 11 in a state ready for use and with a part of the housing cut away, FIG. 13 shows the auto injector of FIG. 12 with the protection cap removed, FIG. 14 shows the auto injector of FIG. 12 with the release member activated, FIG. 15 shows the auto injector of FIG. 12 with the injection trigger member activated, FIG. 16 shows the auto injector of FIG. 12 with the syringe moved to its second position, FIG. 17 shows the auto injector of FIG. 12 with the syringe emptied, FIG. 18 shows the auto injector of FIG. 12 with the release member released, FIG. 19 shows the auto injector of FIG. 12 with the retraction lock released, and FIG. 20 shows the auto injector of FIG. 12 with the syringe retracted.

The figures are schematic and simplified for clarity, and they merely show details, which are essential to the understanding of the invention, while other details have been left out. Throughout, the same reference numerals are used for identical or corresponding parts.

It should be noted that in addition to the exemplary embodiments of the invention shown in the accompanying drawings, the invention may be embodied in different forms and should not be construed as limited to the embodiments set forth herein. Rather, these embodiments are provided so that this disclosure will be thorough and complete, and will fully convey the concept of the invention to those skilled in the art.

FIG. 1 shows an auto injector 10 according to the present invention. It has an elongated housing 12 with a substantially rectangular cross-section for an easy grip by hand. The illustrated embodiment may for example have a length of 10 cm, a width of 3 cm, and a thickness of 1.5 cm. The housing 12 has an opening at one end thereof closed by a removable protection cap 14. At the opposite end of the housing is a trigger button 16 that serves as the injection trigger member as further explained below.

FIG. 2 shows the auto injector of FIG. 1 with a top part of the housing 12 removed. The housing 12 accommodates a syringe 18 with a needle 20 (not visible). The syringe 18 is positioned in a first position with the needle 20 accommodated within the walls of the housing 12.

In the illustrated embodiment, a coil spring 22 serves as the driver for moving the syringe 18 from the first position, in which position the needle is accommodated inside the housing, to a second position in which position the needle protrudes outside the housing. The coil spring 22 is positioned laterally in relation to the syringe 18 and is compressed so that it applies a force between a first arm, i.e. the plunger arm 24, and a second arm, i.e. the shoulder arm 26. One end of the plunger arm 24 abuts the end 28 of the plunger 30 of the syringe 18 while the other end is configured with a first ring 32. A rotatably mounted release shaft 34 extends through the first ring 32. Protrusions or tongues 36 protruding from the release shaft 34 and extending in parallel with the longitudinal axis of the release shaft 34 have end edges abutting the first ring 32 and preventing the ring from moving to the left in FIG. 2 in response to the force exerted by the coil spring 22. Likewise, one end of the shoulder arm 26 is configured with a second ring 38. The release shaft 34 also extends through the second ring 38. Other protrusions or tongues 40 protruding from the release shaft 34 and extending in parallel with the longitudinal axis of the release shaft 34 have end edges abutting the second ring 38 and preventing the second ring 38 from moving to the right in FIG. 2 in response to the force exerted by the coil spring 22. Thus, the end edges of the tongues 40 abutting the second ring 38 form the first anchor location 39.

In FIG. 3, the protection cap 14 has been removed from the auto injector 10 thereby exposing a skin contact button 42 intended to be pressed against the injection site during use and serving as the release member as will be further explained below.

Typically, the syringe 18 also has a rubber cap (not shown) for protection of the needle 20 in which case the protection cap 14 has fingers gripping an edge of the rubber cap so that the rubber cap is removed together with the protection cap 14.

A lock arm 44 has an end that abuts the trigger button 16 so that the user is prevented from depressing the trigger button and thus, from starting automatic injection.

FIG. 4 shows the auto injector 10 with the skin contact button 42 depressed whereby the lock arm 44 is released so that it is no longer kept in a fixed position by the pivotally mounted locking member 46. Depression of the trigger button 16 is now possible. Thus, in accordance with the invention, the auto-injector has a second injection lock configured in a locked state for preventing syringe movement from the first position to the second position by user operation of the injection trigger member and a release member configured for releasing the second injection lock to an unlocked state by first user operation of the release member in which unlocked state the second injection lock does not prevent syringe movement from the first position to the second position by user operation of the injection trigger member. In the illustrated example, first user operation of the release member is constituted by the user pressing the release member against the skin surface at the injection site.

In the illustrated embodiment, the second injection lock comprises the lock arm 44 and the pivotally mounted locking member 46. In the locked state shown in FIG. 3, the second injection lock prevents user operation of the injection trigger member, i.e. the trigger button 16 in the illustrated embodiment, thereby preventing syringe movement from the first position to the second position by user operation of the trigger button 16. The release member, i.e. the skin contact button 42 in the illustrated embodiment, when pressed against the injection site, releases the second injection lock to an unlocked state allowing depression of the trigger button 16 by turning the locking member 46 so that one end thereof abutting an end of the lock arm 44 moves away from the lock arm so that the lock arm 44 can be displaced together with together with the trigger button 16, and thus, no longer prevents the trigger button 16 from being depressed.

FIG. 5 shows the auto injector 10 with both the skin contact button 42 and the trigger button 16 depressed. The trigger button 16 has a protruding flange 48 that abuts a tap 50 protruding from the release shaft 34 perpendicular to its longitudinal axis. When the trigger button 16 is depressed, the protruding flange 48 displaces the tap 50 thereby turning the release shaft 34 an angle of approximately 30° from a first angular position to a second angular position. This turns the tongues 36 of the release shaft 34 into second angular positions fitting corresponding through-going grooves (not visible) inside the first ring 32 of the plunger arm 24. The grooves are sized to accommodate the tongues 36 thereby allowing the ring to slide along the release shaft 34 with the tongues 36 sliding inside the grooves thereby releasing the plunger arm from its fixed position so that the plunger arm 24 is displaced to the left in the Figures in response to the force of the coil spring 22. The moved plunger arm 24 pushes the plunger 30 and thereby the syringe 18 towards its second position.

Thus, in accordance with the invention, the auto injector has a first injection lock configured in a locked state for preventing syringe movement from the first position to the second position and an injection trigger member configured for releasing the first injection lock to an unlocked state by user operation of the injection trigger member in which unlocked state the first injection lock does not prevent the driver from moving the syringe from the first position to the second position.

In the illustrated embodiment, the first injection lock of the illustrated embodiment comprises the release shaft 34 with tongues 36 interacting with the corresponding grooves (not visible) in the first ring 32 of the plunger arm 24. In the locked state, the release shaft 34 has a first angular position in which end edges of the tongues 36 abut the first ring 32 and prevent movement of the plunger arm 24. Depression of the injection trigger member, i.e. the trigger button 16 in the illustrated embodiment, releases the first injection lock by the turn of the release shaft 34 as explained above.

FIG. 6 shows the syringe 18 in its second position wherein the shoulder 52 of the syringe 18 abuts an end of the shoulder arm 26 and an internal protrusion in the housing 12. In the second position of the syringe 18, the needle 20 is exposed through an aperture in the skin contact button 42.

As shown in FIG. 7, the plunger arm 24 continues its movement while the syringe 18 is kept in its second position whereby the syringe 18 is emptied and the medication is injected into the user. The plunger arm 24 is prevented from further movement to the left by abutment with the retraction lock arm 54 which again abuts the pivotable locking member 46 and a guiding protrusion 56 of the skin contact button 42.

Upon injection, the user removes the auto injector 10 from the injection site. During removal from the injection site, the syringe 18 is automatically retracted from its second position so that the needle 20 is withdrawn into the housing 12 and kept within the walls of the housing 12 thereby preventing accidental contact with the needle 20.

In FIG. 8, the auto injector 10 has been removed from the injection site and a resilient member such as a coil spring has forced the skin contact button 42 back to its original position shown in FIGS. 1-3. The corresponding displacement of the guiding protrusion 56 of the skin contact button 42 allows the pivotally mounted retraction lock arm 54 to pivot away from the first ring 32 of the plunger arm 24 in response to the force exerted by the coil spring 22 on first ring 32. Since the first ring 32 abuts a skew edge of the retraction lock arm 54 further movement of the first ring 32 to the left in the Figure is now possible by pivoting the retraction lock arm 54 away from the first ring 32.

This is shown in FIG. 9. Pivoting the retraction lock arm 54 also disconnects the first ring 32 from the remaining part of the plunger arm 24 so that the plunger arm 24 is free to move back to the right together with the syringe 18. Simultaneous with the pivoting of the plunger arm 24 and further explained below, the first ring 32 turns the release shaft 34 an angle whereby the shoulder arm 26 with the second ring 38 is released from its fixed position and since the first ring 32 is now kept in a fixed position at the second anchor location 41, the coil spring 22 urges the second arm, i.e. the shoulder arm 26 with the second ring 38 in the illustrated embodiment, to the right in the Figures and thereby retracts the syringe 18 by its shoulder 52 to its original first position constituting the retracted position of the syringe 18. In the retracted position, the needle 20 is no longer exposed to the surroundings thereby avoiding health hazards and allowing disposal of the used auto injector.

Further turning of the release shaft 34 by the first ring 32 is possible because the length of the tongues 36 is shorter than the displacement of the first ring 32 so that the grooves of the first ring 32 do not accommodate the tongues 36 in the position shown in FIG. 7. Then, the turning of release shaft 34 is obtained in a way similar to the turning of the release shaft 34 by the trigger button 16 as previously explained. Thus, the first ring 32 has an indentation with a skew edge that displaces a second tap (not visible) protruding from the release shaft 34 perpendicular to its longitudinal axis during its final movement towards the left of FIG. 7 thereby turning the release shaft 34 another 30°. This causes the tongues 40 at the right end of the release shaft 34 to be turned and aligned with corresponding through-going grooves in the second ring 38 of the shoulder arm 26. The grooves (not visible) are sized to accommodate the tongues 40 so that movement of the shoulder arm 26 to the right of the Figure is made possible and thus, the coil spring 22 urges the shoulder arm 26 abutting the shoulder 52 of the syringe 18 to the right thereby retracting the syringe 18 back into its first position as shown in FIG. 10.

Thus, in accordance with the invention, the auto injector comprises a retraction lock for prevention of retraction of the syringe in a locked state of the retraction lock. In the illustrated embodiment, the retraction lock comprises the locking member 46, the guiding protrusion 56, the retraction lock arm 54, and the release shaft 34 with the tongues 40. The release member, i.e. the skin contact button 42 in the illustrated embodiment, is configured for releasing the retraction lock to an unlocked state by second user operation of the release member, i.e. removal of the auto injector from the injection site thereby releasing the skin contact button 42 from its depressed position to its original position. In its original position, the guiding protrusion 56 is displaced a distance from the retraction lock arm 54 so that the retraction lock arm can turn away from the first ring 32 allowing further movement of the first ring 32 to the left releasing the shoulder arm for movement to the right as explained above.

Upon removal of the auto injector 10 from the injection site, it is not possible to depress the skin contact button 42 again.

It should be noted that the auto injector may be constructed for making injections in more than one step. For example, in a dual chamber syringe, one chamber may contain freeze-dried medicine and a second chamber may contain liquid to be mixed with the freeze-dried medicine. A first actuation of the auto injector may lead to breakage of a seal between the first and second chambers bringing the liquid in contact with the freeze-dried medicine and a second actuation may lead to injection of the mixed medicine. For example, the release shaft 34 in the illustrated embodiment may contain more than two sets of tongues to be aligned with corresponding grooves in the respective rings 32, 38 at respective different angular positions of the release shaft 34 thereby allowing one of the rings 32, 38 to be displaced a predetermined distance when the release shaft 34 has a specific angular position. This makes it possible to use medicine without preservatives which again makes the auto injector more user friendly because most of the pain caused by injections is caused by preservatives in the wound.

It should further be noticed that utilization of a rotatable shaft for controlling displacement of parts in the auto injector by locking the position of specific parts in one angular position of the shaft and unlocking the position in another angular position of the shaft makes the device more resistant to the user dropping the device.

In prior art devices, locking and unlocking displacement of parts in the auto injector by linear movement of locking parts is inherently sensitive to dropping of the device, since such dropping may induce a linear movement of parts in the device, e.g. causing inadvertent triggering of the device. In the auto injector according to the invention, dropping of the device will not cause rotation of the rotatable shaft, and since the auto injector can not be dropped on the injection trigger member and the release member simultaneously, the device will not inadvertently be triggered by dropping of the device.

FIGS. 11-20 correspond to FIGS. 1-10, respectively, and illustrate the operation of another auto injector according to the invention operating in a way similar to the auto injector illustrated in FIGS. 1-10 and explained above.

The invention claimed is:

1. An auto injector with a housing for accommodation of a syringe with a needle, the syringe being movably positioned in the housing between a first position in which position the needle is accommodated inside the housing and a second position in which position the needle protrudes outside the housing,
a mechanical driver anchored to the housing at a first anchor location for applying a first force to the syringe thereby moving the syringe from the first position to the second position,
characterized in that
the mechanical driver is also configured for applying a second force to the syringe by anchoring the mechanical driver to a different second anchor location,
and that the auto injector further comprises a first arm configured for conveying the first force from the mechanical driver to the syringe for moving the syringe from the first position to the second position, and a second arm configured for conveying the second force from the mechanical driver to a syringe shoulder for retracting the syringe from the second position to the retracted position, and
wherein the mechanical driver has one end applying the first force to the first arm and another end applying the second force to the second arm, and wherein the second arm is kept in a fixed position during movement of the syringe from the first position to the second position, and wherein the first arm is kept in a fixed position during movement of the syringe from the second position to the retracted position.

2. An auto injector according to claim 1, wherein the mechanical driver is configured for moving the syringe from the second position to a retracted position in which position the needle is accommodated inside the housing, when the mechanical driver is anchored to the second anchor location.

3. An auto injector according to claim 1, wherein the mechanical driver is positioned laterally with relation to the syringe.

4. An auto injector according to claim 1, wherein the mechanical driver is a spring.

5. An auto injector according to claim 4, wherein the mechanical driver is a coil spring.

6. An auto injector according to claim 1, further comprising a rotatable release shaft configured for rotation between a first angular position in which position the shaft prevents movement of the syringe from the first position to the second position and a second angular position in which position the shaft does not prevent movement of the syringe from the first position to the second position.

7. An auto injector according to claim 6, wherein the rotatable release shaft is positioned laterally in relation to the syringe.

8. An auto injector according to claim 6, wherein the mechanical driver is a coil spring that is arranged coaxially with the rotatable release shaft.

9. An auto injector according to claim 6, wherein an injection trigger member is coupled to the rotatable release shaft and configured to turn the release shaft from the first angular position to the second angular position by user operation.

10. An auto injector according to claim 9, wherein the injection trigger member has a flange that abuts a tap protruding from the release shaft perpendicular to the longitudinal axis of the release shaft in such a way that movement of the injection trigger member with the flange displaces the tap thereby turning the release shaft an angle from the first angular position to the second angular position.

11. An auto injector according to claim 6, wherein the release shaft is further configured for rotation between a third angular position in which position movement of the syringe from the second position to the retracted position is prevented and a fourth angular position in which position movement of the syringe from the second position to the retracted position is not prevented.

12. An auto injector according to claim 1, wherein the first arm has a first ring positioned in such a way that a release shaft extends through the first ring, and wherein the release shaft has first tongues protruding from the release shaft and extending in parallel with the longitudinal axis of the release shaft with end edges abutting the first ring in one angular position of the release shaft thereby preventing the first ring from moving in the direction of the first tongues in response to the force applied to the first arm by the mechanical driver.

13. An auto injector according to claim 12, wherein the first ring has through-going grooves in its inner circular circumferential surface abutting the release shaft positioned in such a way that the first tongues of the release shaft in another angular position of the release shaft fit respective through-going grooves in the inner circular circumferential surface of the first ring, the grooves being sized to accommodate the tongues thereby allowing the first ring to slide along the release shaft with the tongues sliding in the grooves so that the first ring can be displaced in the direction of the first tongues in response to the force applied to the first arm by the mechanical driver.

14. An auto injector according to claim 12, wherein the second arm has a second ring positioned in such a way that a release shaft extends through the second ring, and wherein the release shaft has second tongues protruding from the release shaft and extending in parallel with the longitudinal axis of the release shaft and displaced along the longitudinal axis of the release shaft in relation to the first tongues and having end edges abutting the second ring in the other angular position of the release shaft thereby preventing the second ring from moving in the direction of the second tongues in response to the force applied to the second arm by the mechanical driver.

15. An auto injector according to claim 14, wherein the second ring has through-going grooves in its inner circular circumferential surface abutting the release shaft positioned in such a way that the second tongues of the release shaft in a third angular position of the release shaft fit respective through-going grooves in the inner circular circumferential surface of the second ring, the grooves being sized to accommodate the second tongues thereby allowing the second ring to slide along the release shaft with the second tongues sliding in the grooves so that the second ring can be displaced in the direction of the second tongues in response to the force applied to the second arm by the mechanical driver.

\* \* \* \* \*